United States Patent [19]

Kouwenhoven et al.

[11] Patent Number: 5,334,781
[45] Date of Patent: Aug. 2, 1994

[54] PROCESS FOR THE PREPARATION OF NITROBENZENE

[75] Inventors: Herman W. Kouwenhoven, Herrliberg; Leopoldo Bertea; Roel Prins, both of Zürich, all of Switzerland

[73] Assignee: CU Chemie Uetikon AG, Uetikon, Switzerland

[21] Appl. No.: 5,104

[22] Filed: Jan. 15, 1993

[30] Foreign Application Priority Data

Jan. 15, 1992 [CH] Switzerland ............... 0101/92-5

[51] Int. Cl.$^5$ ................................. C07C 205/06
[52] U.S. Cl. ............................. 568/927; 568/932
[58] Field of Search ........................ 568/932, 927

[56] References Cited

U.S. PATENT DOCUMENTS

| | | | |
|---|---|---|---|
| Re. 33,549 | 5/1991 | Weigert | 564/409 |
| 3,966,830 | 6/1976 | Shimada et al. | 568/937 |
| 4,107,220 | 8/1978 | Owsley et al. | 568/937 |
| 4,371,721 | 2/1983 | Wu | 568/946 X |
| 4,415,744 | 1/1983 | Schumacher et al. | 560/20 |
| 4,418,230 | 1/1983 | Bakke et al. | 568/940 |
| 4,754,083 | 6/1988 | Reith et al. | 568/932 |
| 4,891,448 | 1/1990 | Garces et al. | 568/628 |
| 5,194,244 | 3/1993 | Brownscombe et al. | 423/700 |

FOREIGN PATENT DOCUMENTS

| | | |
|---|---|---|
| 0078247 | 5/1983 | European Pat. Off. . |
| 0092372 | 10/1983 | European Pat. Off. . |
| 0317907 | 5/1989 | European Pat. Off. . |
| 0343048 | 11/1989 | European Pat. Off. . |

*Primary Examiner*—Robert L. Stoll
*Assistant Examiner*—Valerie Fee
*Attorney, Agent, or Firm*—Fisher & Associates

[57] ABSTRACT

The invention concerns a process for the preparation of nitrobenzene from benzene and nitric acid, wherein catalysts are applied based on the zeolite clinoptilolite.

5 Claims, No Drawings

PROCESS FOR THE PREPARATION OF NITROBENZENE

This invention relates to the zeolite clinoptilolite and its application as a catalyst in the gasphase nitration of benzene to nitrobenzene using nitric acid as a nitrating agent. Processes for the gasphase nitration of aromatics in which $NO_2$ or other nitrogen oxides are applied as nitrating agents have been mentioned in the relevant literature. A review presented in U.S. Pat. No. 4,754,083 shows that a large variety of materials has been claimed as catalysts in the gasphase nitration of aromatics using nitrogen oxides as nitrating agents. In the review in U.S. Pat. No. 4,754,083 zeolites and other crystalline or amorphous aluminosilicates are frequently mentioned as particular effective catalysts.

In U.S. Pat. No. 4,754,083 molecular sieves, montmorillonite and pillared bentonite are claimed in general as catalysts in thee gasphase nitration of substituted aromatics containing a meta directing group such $NO_2$. Experiments e described concerning the gasphase nitration of nitrobenzene using catalysts based on a large number of different zeolites, such as Zeolon 900H; H-Y; H-Bern: H-ZSM-5 and H-erionite. In these experiments both a fixed bed and a fluidized bed reactor were used, and the results the conversion obtained after one to two hours reaction time is reported. The data are accordingly not sufficient to assess the stability of the catalysts in experiments of longer duration. The preferred catalysts, which were based on zeolite Na-X and H-ferrierite, had a low conversion activity (<25%) and a high selectivity for the formation of p-dinionzene A gasphase process for the manufacture of nitrobenzene using nitric acid as nitrating agent is proposed EPA 343.048, acidic layered silicates and/or acidic oxidic materials are applied catalysts. The latter consist of oxides of group IVA of the periodic system in combination with one or more of the following oxides: tungsten trioxide, molybdenum trioxide or zinc oxide. The perfomance of the catalysts described in EPA 343.048 is said to be very good and moreover stability, activity and selectivity of the claimed materials is supposedly better than those of other materials which were described in earlier publications and/or patents.

The application of catalysts based on H-mordenite in the gasphase nitration of aromatics using resp. $NO_2$, $N_2O_3$ or $N_2O_4$ and preferentially $NO_2$, as nitrating agent is described in a patent series comprising a.o. EP 53.053; EP 78.247; EP 92.372 and U.S. Pat. No. 4,107,220. The mordenite based catalysts as described in these patents are commercial products, which were available from the Norton Cy under the Tradename "Zeolon-x00H, e.g. Zeolon 900H or Zeolon 200H. In the descriptions given in the patents mentioned earlier in this paragraph the materials are preferentially pretreated at reaction conditions with the nitrating agent and further no additional pretreatment is considered as beneficial for catalyst performance.

In DEOS 28.26.433 and U.S. Pat. No. 4.418.230, the gasphase nitration of toluene with nitric acid is described using Zeolon 200H as a catalyst. Also in these patents no further pretreatment leading to an improved catalyst performance is mentioned, experiments were carried out at 473 K., atmospheric pressure and a toluene/nitric acid molar ratio of about 1.4. No data were presented relating to the stability of the performance of the mordenite based catalyst. In fact most of the experimental results relate to the application of a catalyst based on montmorillonite, which had a much better performance than the mordenite based catalyst Our copending CH Patent application nr 03 554/91-6 relates to the application of catalysts based on mordenite in the gasphase nitration of benzene and the effects of the various activation methods, which may be applied in the preparation of mordenite based catalysts. During further studies with other zeolitic materials we have surprisingly found that the zeolite clinoptilolite is a good starting material for the preparation of very efficient catalysts for the gasphase nitration of benzene using nitric acid as a nitrating agent.

Clinoptilolite is a molecular sieve zeolite, which occurs widely in the earth's crust as a mineral deposit. The chemical composition of clinoptilolites is not constant but depends on the location of the deposit of the mineral. The crystallographic structure of clinoptilolite is described in the "Atlas of Zeolitic Structure Types" by W. M. Meier and D. H. Olson, 2nd edition, published by Butterworth in 1987 on behalf of the Structure Commission of the International Zeolite Association. Further data on structure and properties of clinoptilolites are for instance found in an article by M. W. Ackley and R. T. Yang in AIChE Journal 37, (1991), 1645. The clinoptilolite lattice has, due to the substitution of four valent silicon atoms by trivalent aluminum atoms, a negative electric charge, which is compensated by the exchangeable atoms. In many applications of zeolites in catalysis acidic zeolites are used, which are usually described as H-zeolites. H-clinoptilolite may be prepared by ion-exchange processes, either direct with acids or indirect via ion-exchange with an ammonium salt followed by calcination for removal of ammonium.

The catalytic gasphase nitration of aromatics according to the present invention is carried out using catalysts based on clinoptilolite. Catalysts are prepared from clinoptilolite by the combined application of ion-exchange and calcination. As a result of these treatments exchangeable cations are firstly completely or partially removed and replaced by protons and secondly Al atoms are removed from their crystallographic positions in the clinoptilolite lattice and presumably replaced by Si atoms. The sites of the Al and Si atoms in the lattice of a zeolite such as clinoptilolite are commonly described as T-sites, which is an abbreviation for lattice positions having a tetrahedral oxygen coordination.

According to the present invention the catalytic nitration of aromatics is carried out at a temperature between 300 and 623 K., preferably at a temperature between 323 and 523 K., using as a nitrating agent nitric acid, having a $HNO_3$ content higher than 15% wt, more preferentially having a $HNO_3$ content higher than 50% wt, and as catalysts materials based on the zeolite clinoptilolite are applied.

The invention is illustrated by examples in the following paragraphs. The preparation of some catalysts based on mordenite is illustrated in example 1. The preparation of catalysts based on clinoptilolite is described in examples 2 and 3. Testing of the so prepared catalysts and that of Zeolon 900H is described in examples 4 through 11.

PREPARATION OF THE CATALYSTS

EXAMPLE 1

Catalysts were prepared starting from commercial mordenite, type PM1-Na, available from CU Chemie Uetikon. Analytical data may be found in Table 1. The material was subjected to the following activation procedure: 500 g of PM1-Na was slurried in 5000 ml of a 1 molar solution of HCl in water and while stirring the slurry was heated for one hour at 373 K. The solids were filtered off and subsequently washed with 5000 ml of demineralized water. The filtercake was dried in air during one hour at 373 K., the dried material is sample A. 100 g of sample A was slurried in 1000 ml of a 1 molar solution of $NH_4NO_3$ in water and the stirred slurry was heated during one hour at 373 K. The solids were subsequently filtered off and washed with 1000 ml of demineralized water. The product was again slurried in 1000 ml of a 1 molar $NH_4NO_3$ solution in water and the stirred slurry was heated at 373 K. for one hour. The solids were subsequently filtered off and washed with 1000 ml demineralized water. A first part of the filtercake was dried in air during 16 hours at 393 K. and subsequently calcined in an open crucible at 773 K. during 3 hours, the product is sample B; a second part of the filtercake was calcined for 5 hours at 823 K. in a covered crucible, the product is sample C; a third part of the filtercake was calcined during 5 hours at 973 K., the product is sample D. Analytical data on the samples B,C and D are collected in Table 1.

EXAMPLE 2

In the preparation of catalysts based on clinoptilolite a sample commercial clinoptilolite, Type Clino MH was used, this material is obtainable from CU Chemie Uetikon. The average size of the clinoptilolite crystals in this material is smaller than 500 nm, and the crystals are agglomerated to larger, physically strong particles. Additional analytical data are given in Table 1. The ammonium form of clinoptilolite was prepared as follows: 150 g Clino MH was slurried in 500 ml of a 1 molar aqueous $NH_4NO_3$ solution and heated during one hour at 373 K. while stirring. The solids were filtered off and washed with 1000 ml demineralized water. The filtercake was reslurried in 500 ml of a 1 molar aqueous $NH_4NO_3$ solution and heated during one hour at 373 K. while stirring. The solids were filtered off and washed with 1000 ml demineralized water. The filtercake was reslurried in 500 ml of a 1 molar aqueous $NH_4NO_3$ solution and heated during one hour at 373 K. while stirring. The solids were filtered off and washed with 1000 ml demineralized water. The filtercake was dried during 85 hours in air at 433 K., and subsequently for 3 hours calcined in air at 823 K., spread in a thin layer in a flat crucible. (shallow bed calcination). The calcined product is sample E, analytical data are collected in Table 1.

EXAMPLE 3

150 g of Clino MH was slurried in 500 ml of an aqueous 1 molar $H_2SO_4$ solution and the slurry was heated during 1 hour at 373 K. while stirring. The solids were filtered off and washed with 1000 ml demineralized water. The filtercake was again slurried in 500 ml of an aqueous 1 molar $H_2SO_4$ solution and the slurry was heated during 1 hour at 373 K. while stirring. The solids were filtered off and washed with 1000 ml demineralized water. The product was 85 hours dried in air at 433 K., the dried product is sample F. Part of sample F was subsequently for 3 hours calcined in air at 823 K., spread in a thin layer in a flat crucible. (shallow bed calcination). The calcined product is sample G, analytical data are collected in Table 1.

TABLE 1

| Sample | Molar ratio $SiO_2/Al_2O_3$ | $Na_2O$ wt % | Surface area*, ($m^2/g$) Total | Outer | Pore Volume (ml/g) Micropores |
|---|---|---|---|---|---|
| 900H | 10 | 0.75 | 460 | 59 | 0.17 |
| PM1-Na | 12.4 | 7.16 | 168 | — | — |
| B | 12.5 | <0.01 | 480 | 61 | 0.20 |
| C | 12.5 | <0.01 | 490 | 60 | 0.20 |
| D | 12.5 | <0.01 | 495 | 85 | 0.19 |
| Clino MH | 10.7 | 3.25 | 65 | 30 | 0.01 |
| E | 12.6 | 0.45 | 318 | 60 | 0.11 |
| F | 17.3 | <1 | 325 | 71 | 0.13 |
| G | 17.3 | <1 | 211 | 77 | 0.07 |

*measured with $N_2$ using a "Micromeretics ASAP 2000M" and standard procedures.

Catalyst testing procedure The nitration of benzene was carried out in continuous gasphase experiments, during at least 20 hours, the following conditions were apllied:

| WHSV benzene | 1 kg.kg.$^{-1}$h$^{-1}$ |
|---|---|
| WHSV nitric acid* | 0.4 kg.kg.$^{-1}$h$^{-1}$ |
| Temperature | 443 K |
| Pressure | atmospheric |

*calculated as 100% wt nitric acid

Nitrogen was used as a carrier gas; the volume ratio carrier gas/benzene(g) was about 1.34. The partial pressures in mbar of the various components in the gaseous mixture were: Nitric acid: 138; benzene: 281; water: 256; carrier gas: 385.

Before use in the tests the materials were broken in order to obtain a 0.4–0.9 mm sieve fraction. Before being loaded into the reactor the catalysts were either precalcined at 773 K. followed by an equilibration in ambient air or they were loaded into the reactor without any pretreatment, other than the catalyst preparation procedure described earlier. Catalysts were in situ pretreated with carrier gas during two hours at reaction temperature, subsequently nitric acid was passed over the catalyst during 0.5 hour, at reaction conditions, as a result of this step an increase in temperature was usually observed. The optimal duration of the pretreatment with nitric acid vapour depends on the reaction conditions and is preferentially sufficiently long to saturate the catalyst with nitric acid under the prevailing conditions. Upon equilibration with nitric acid benzene was introduced in the feed stream, which resulted in a second exothermic effect supposedly due to the excess nitric acid on the catalyst. After a line-out period of one hour the reaction product was collected in a trap cooled to 278 K. and filled with acetone. The composition of the organics in the product was periodically analyzed by a conventional GC method and the non converted nitric acid was determined by titration.

EXAMPLE 4 THROUGH 11

The testprocedure described above was applied to measure the catalytic activity of the following materials: Example 4: Norton Zeolon 900H; example 5: sample B; example 6: sample C; example 7: sample D; example 8: Clino MH; example 9: sample E; example 10: sample F; example 11: sample G. Results of these experiments are collected in table 2, all experiments were run for at least 20 hours.

TABLE 3

| | Examples 4 through 11 | | | | | | | |
|---|---|---|---|---|---|---|---|---|
| | Example nr | | | | | | | |
| | 4 | 5 | 6 | 7 | 8 | 9 | 10 | 11 |
| Selectivity on nitric acid ((%) | 99 | 90 | 90 | 96/99 | 92 | 99+ | 93 | 89/94 |
| Nitrobenzene yield on nitric acid in (%)* | 27/10 | 69 | 70 | 70/36 | 64/61 | 82/81 | 74/71 | 55/45 |

*in case of catalyst deactivation, the first value represents the number at runhour 3 and the second value refers to runhour 20.

The data in Table 2 show that Norton Zeolon 900H has a medium activity and a poor stability. and that the performance of catalysts based on mordenite in the gasphase nitration of benzene is strongly dependent on the method of catalyst preparation. Catalysts based on clinoptilolite are more active than those based on mordenite and show a high selectivity at high conversion. The performance of the clinoptilolite based catalysts depends however strongly on their preparation method.

What is claimed is:

1. A process for the preparation of nitrobenzene, characterized by the catalytic nitration of benzene at a temperature between 300 and 523 K., using aqueous nitric acid as nitrating agent and a catalyst based on H-clinoptilolite.

2. A process according to claim 1, characterized by an average H-clinoptilolite crystal size smaller than 1000 nm.

3. A process according to claim 1 characterized by the use of a nitrating agent consisting of aqueous nitric acid, having a nitric acid concentration above 50 wt %.

4. A process according to claim 1 characterized by the application of reaction conditions leading to a gasphase process for the nitration of benzene.

5. A process according to claim 4, characterized by a reaction temperature between 423 and 523 K.

* * * * *